US00PP10056P

United States Patent [19]

Polys

[11] Patent Number: Plant 10,056

[45] Date of Patent: Oct. 7, 1997

[54] CHRYSANTHEMUM PLANT NAMED 'GOLDEN PHOENIX'

[75] Inventor: Susan M. Polys, Salinas, Calif.

[73] Assignee: Yoder Brothers, Inc., Barberton, Ohio

[21] Appl. No.: 605,617

[22] Filed: Feb. 22, 1996

[51] Int. Cl.[6] ..... A01H 5/00

[52] U.S. Cl. ..... Plt./78

[58] Field of Search ..... Plt./78, 82.2

[56] References Cited

U.S. PATENT DOCUMENTS 4,616,099 10/1986 Sparkes ..... 47/58

OTHER PUBLICATIONS

Broertjes, et al., 1980, "A Mutant of a Mutant of a . . . Irradiation of Progressive Radiation–induced Mutants in a Mutation Breeding Programme With *Chrysanthemum morifolium*", Euphytica, 29:525–530.

Gosling, ed., 1979, "The Chrysanthemum Manual—6th Edition", The National Chrysanthemum Society, Essex Telegraph Press Ltd., London, pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X– and Gamma Radiation", Euphytica, 15: 204–210.

*Primary Examiner*—Howard J. Locker
*Attorney, Agent, or Firm*—Foley & Lardner

[57] ABSTRACT

A Chrysanthemum plant named Golden Phoenix particularly characterized by its flat capitulum form; quilled decorative capitulum type; golden-yellow ray floret color; diameter across face of capitulum of 114 to 140 mm when fully opened, when grown as a pinched disbudded pot mum; photoperiodic flowering response of 50 to 57 days after start of short days; plant height, with 21 long days after sticking unrooted cuttings and with 1 to 2 applications of 2500 ppm B-9 SP ranges from 23 to 33 cm when grown as a pinched pot mum with 4 cuttings in a 15 cm pot; branching pattern is spreading, each plant having 4 to 5 laterals after pinch; and recommended as a disbudded pot mum.

1 Drawing Sheet

The present invention comprises a new and distinct cultivar of Chrysanthemum, botanically known as *Dendranthema grandiflora*, and referred to by the cultivar name Golden Phoenix.

Golden Phoenix, identified as 6864 (90-728D05), is a product of a mutation induction program. The new cultivar was discovered and selected by inventor Susan M. Polys on Sep. 14, 1992 in a controlled environment in Salinas, Calif. as one flowering plant within a flowering block established as rooted cuttings from stock plants which had been exposed as unrooted cuttings to an X-ray source of 1750 rads in Fort Myers, Fla. on Mar. 19, 1992. The irradiated parent cultivar was the cultivar Phoenix, disclosed in U.S. Plant Pat. No. 8,843, and described as a flat quilled decorative disbud pot mum with a soft apricot-ivory flower color with slightly darker center of the flower.

The irradiation program resulting in Golden Phoenix had as its primary objective the expansion of color ranges of the parent cultivar. The irradiation program comprised irradiation of cuttings of the parent cultivar at irradiation levels of 1500, 1750 and 2000 rads. A total of 1337 cuttings harvested from a total of 225 irradiated plants were planted on Jul. 6, 1992. Of these, 13 initial selections were made, which selections were then revegetated and reflowered. One selection died in the revegetation process. Three consecutive flowerings resulted in discarding 10 of the original selections on May 18, 1993. Two selections were reselected on May 18, 1993, prior to discarding the original selections. The 2 remaining selections and the 2 reselections were maintained as PIs (Possible Introductions) and further trialed in Salinas, Calif. and Leamington, Ontario, Canada, ultimately resulting in discarding one selection and one reselection on May 10, 1994, discarding one reselection on May 31, 1994 and the decision to introduce the one remaining selection as Golden Phoenix.

The first act of asexual reproduction of Golden Phoenix was accomplished when vegetative cuttings were taken from the initial selection in November of 1992 in a controlled environment in Salinas, Calif., by technicians working under supervision of Susan M. Polys.

Horticultural examination of controlled flowerings of successive plantings has shown that the unique combination of characteristics as herein disclosed for Golden Phoenix are firmly fixed and are retained through successive generations of asexual reproduction.

Golden Phoenix has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Golden Phoenix, which, in combination, distinguish this Chrysanthemum as a new and distinct cultivar:

1. Flat capitulum form.
2. Quilled decorative capitulum type.
3. Golden-yellow ray floret color.
4. Diameter across face of capitulum of 114 to 140 mm when fully opened, when grown as a pinched disbudded pot mum.
5. Photoperiodic flowering response of 50 to 57 days after start of short days.
6. Plant height, with 21 long days after sticking unrooted cuttings and with 1 to 2 applications of 2500 ppm B-9 SP ranges from 23 to 33 cm when grown as a pinched pot mum with 4 cuttings in a 15 cm pot.

7. Branching pattern is spreading, each plant having 4 to 5 laterals after pinch.

8. Recommended as a disbudded pot mum.

The accompanying photographic drawing is a side view of Golden Phoenix, grown as a disbudded pot mum with 4 cuttings in a 15 cm pot, with the colors being as nearly true as possible with illustrations of this type.

Of the commercial cultivars known to the inventor, the most similar in comparison to Golden Phoenix is the parent cultivar Phoenix. All traits of Golden Phoenix are similar to those of Phoenix, except for the ray floret color. The ray floret color of Golden Phoenix is golden-yellow (R.H.S. 9C), while the ray floret color of Phoenix is described as soft apricot-ivory (R.H.S. between 11D and 13D) with slightly darker center of the flower (R.H.S. 20C to 20D).

In the following description color references are made to The Royal Horticultural Society Colour Chart. The color values were determined on plant material grown as a pinched pot mum with 4 cuttings in a 15 cm pot in Salinas, Calif. on May 18, 1995.

Classification:

*Botanical.*—*Dendrathema grandiflora* cv Golden Phoenix.

*Commercial.*—Flat quilled decorative disbud pot mum.

Inflorescence

A. Capitulum:

*Form.*—Flat.

*Type.*—Quilled decorative.

*Diameter across face.*—114 to 140 mm when fully opened.

B. Corolla of ray florets:

*Color (general tonality from a distance of three meters).*—Golden-yellow.

*Color (upper surface).*—9C.

*Color (under surface).*—9C.

*Shape.*—Straight, quilled.

C. Corolla of disc florets:

*Color (mature).*—14B.

*Color (immature).*—144A to 144B.

D. Reproductive organs:

*Androecium.*—Present on disc florets only; scant pollen.

*Gynoecium.*—Present on both ray and disc florets.

Plant

A. General Appearance:

*Height.*—23 to 33 cm when grown as a pinched pot mum with 21 long days after sticking unrooted cuttings prior to start of short days and with 1 to 2 applications of 2500 ppm B-9 SP.

*Branching pattern.*—Spreading, with 4 to 5 laterals after pinch.

B. Foliage:

*Color (upper surface).*—147A.

*Color (under surface).*—147B.

*Shape.*—Lobed and serrated.

What is claimed is:

1. A new and distinct Chrysanthemum plant named Golden Phoenix, as described and illustrated.

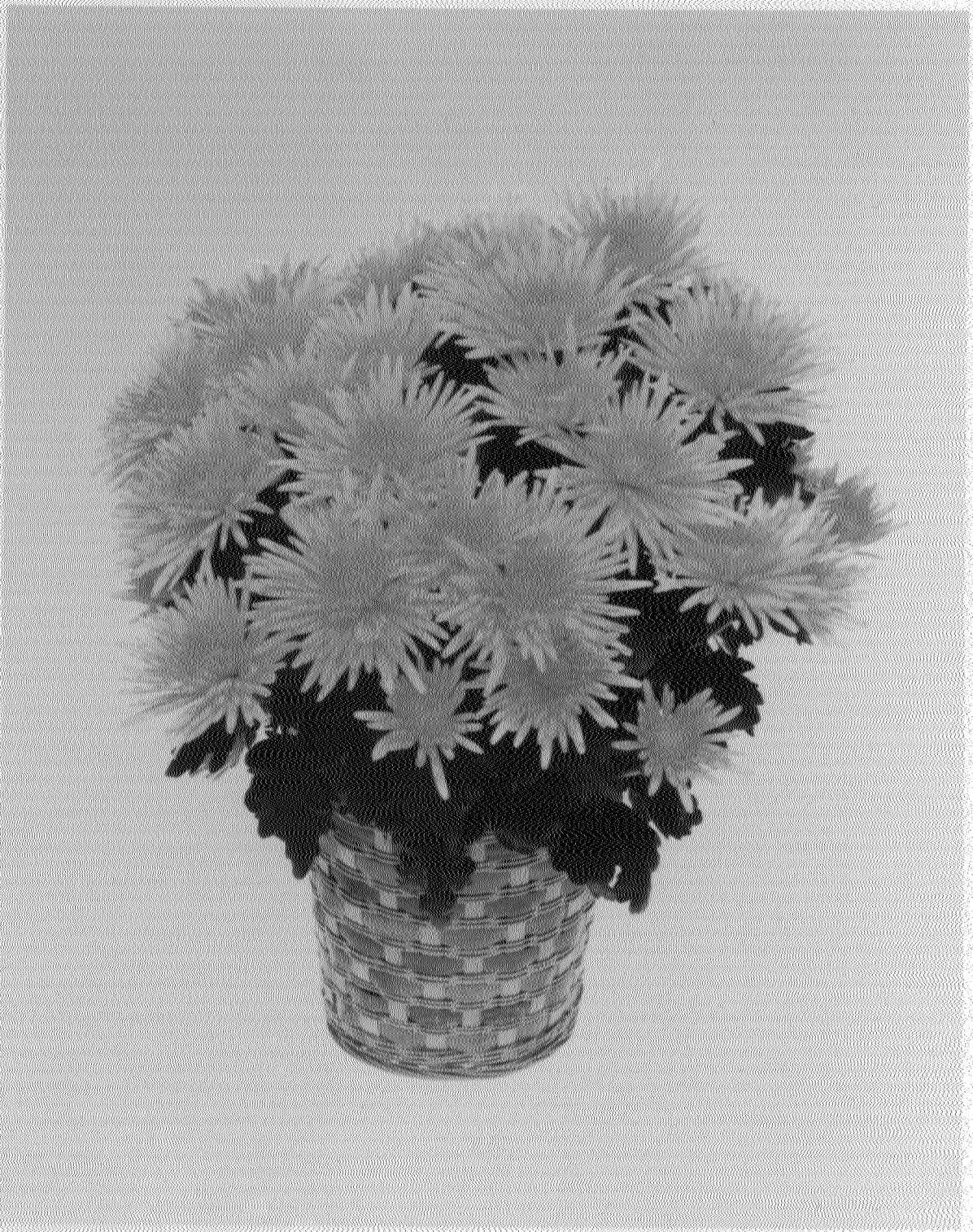

* * * * *